US009069048B2

(12) United States Patent
Cull et al.

(10) Patent No.: US 9,069,048 B2
(45) Date of Patent: Jun. 30, 2015

(54) BROADBAND DECOUPLING PULSE TRAINS WITH INTERLEAVED PAUSES FOR MAGNETIC RESONANCE SPECTROSCOPY

(75) Inventors: Thomas S. Cull, Wickliffe, OH (US); William McLemore, Lakewood, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1043 days.

(21) Appl. No.: 13/141,089

(22) PCT Filed: Nov. 23, 2009

(86) PCT No.: PCT/IB2009/055289
§ 371 (c)(1),
(2), (4) Date: Jun. 21, 2011

(87) PCT Pub. No.: WO2010/073145
PCT Pub. Date: Jul. 1, 2010

(65) Prior Publication Data
US 2011/0267052 A1   Nov. 3, 2011

Related U.S. Application Data

(60) Provisional application No. 61/139,781, filed on Dec. 22, 2008.

(51) Int. Cl.
*G01R 33/46* (2006.01)
*G01N 24/08* (2006.01)
(Continued)

(52) U.S. Cl.
CPC .......... *G01R 33/4608* (2013.01); *G01N 24/088* (2013.01); *G01R 33/3614* (2013.01); *G01R 33/4633* (2013.01); *G01R 33/4836* (2013.01)

(58) Field of Classification Search
USPC .......................... 324/300–322; 600/407–435; 382/128–131
See application file for complete search history.

(56) References Cited

U.S. PATENT DOCUMENTS 4,701,708 A * 10/1987 Hardy et al. ................... 324/311
4,703,270 A * 10/1987 Hall et al. ...................... 324/309
(Continued)

FOREIGN PATENT DOCUMENTS

WO   WO 2010073145 A1 * 7/2010

OTHER PUBLICATIONS

By A. J. Shaka et al: "NMR Broadband Decoupling With Low Radiofrequnecy Power" Journal of Magnetic Resonance, Academic Press, London, GB, vol. 52, No. 1, Mar. 1, 1983, XP023962157 ISSN: 0022-2364 [retrieved on Mar. 1, 1983] p. 159-163.
(Continued)

*Primary Examiner* — Melissa Koval
*Assistant Examiner* — Tiffany Fetzner

(57) ABSTRACT

A magnetic resonance apparatus includes a magnet that generates a static magnetic field, e.g., 7T, and a resonance excitation system that induces resonance in an observed nuclear species such as $^{13}C$ or $^{31}P$. A decoupling delay generator introduces pauses between adjacent pulses of a decoupling pulse train configured to decouple a coupled species such as $^1H$. An RF amplifier whose energy shortage capacity would be exceeded by the pulse train without the pauses amplifies the pulse train with the pauses. The pauses are sufficiently short that decoupling and Nuclear Overhauser Effect enhancement are not adversely affected, but long enough to provide recovery time to the RF amplifier, e.g., 0.2 msec.

19 Claims, 5 Drawing Sheets

Nuclear Overhauser Effect (NOE) sequence based on the WALTZ 16 sequence but with short pauses between each block pulse within a supercycle and longer pauses between supercycles

(51) Int. Cl.
*G01R 33/36* (2006.01)
*G01R 33/483* (2006.01)

(56) References Cited

U.S. PATENT DOCUMENTS

| | | | |
|---|---|---|---|
| 4,959,612 A | | 9/1990 | Luyten |
| 5,043,664 A | | 8/1991 | Kunz |
| 5,196,795 A | * | 3/1993 | Bodenhausen et al. ........ 324/309 |
| 5,229,718 A | | 7/1993 | Cory |
| 5,581,182 A | * | 12/1996 | Fu et al. ........................ 324/309 |
| 6,472,870 B1 | | 10/2002 | Bendall et al. |
| 6,958,604 B2 | * | 10/2005 | An et al. ........................ 324/303 |
| 7,598,738 B2 | * | 10/2009 | Kupce ............................ 324/307 |
| 7,626,386 B2 | * | 12/2009 | Bodenhausen et al. ........ 324/307 |
| 7,948,235 B2 | * | 5/2011 | Foxall ............................ 324/307 |
| 2003/0224533 A1 | * | 12/2003 | Massefski, Jr. ................ 436/518 |
| 2004/0257075 A1 | * | 12/2004 | An et al. ........................ 324/303 |
| 2009/0039883 A1 | * | 2/2009 | Bodenhausen et al. ........ 324/307 |
| 2009/0096449 A1 | * | 4/2009 | Foxall ............................ 324/311 |
| 2009/0224760 A1 | * | 9/2009 | Kupce ............................ 324/311 |
| 2010/0315083 A1 | * | 12/2010 | Pauli et al. ..................... 324/309 |
| 2011/0267052 A1 | * | 11/2011 | Cull et al. ...................... 324/307 |

OTHER PUBLICATIONS

By J. W. M. Jacobs et al: "Broadband Heteronuclear Decoupling" Journal of Magnetic Resonance, Academic; Press, London, GB, vol. 51, No. 1, Jan. 1, 1983, XP023957893 ISSN: 0022-2364 [retrieved on Jan. 1, 1983] (abstract) p. 56-66.

By L. Delevoye et al: "Resolution Enhancement Using a New Multiple-Pulse Decoupling Using Sequence for Quadrupolar Nuclei" Journal of Magnetic Resonance, Academic Press, Orlando, FL, US, vol. 186, No. 1, Apr. 26, 2007, XP022056080 ISSN: 1090-7807 pp. 94-99.

By A.J. Shaka A J et al: "Evaluation of a a New Braodband Decouplong Sequence: Waltz-16" Journal of Magnetic Resonance, Academic Press, London, GB, vol. 53, No. 2, Jun. 15, 1983, XP023956259 ISSN: 0022-2364 [retrieved on Jun. 15, 1983] the whole document, pp. 313-340.

By S. Xu et al: "Inverse Polarization Transfer for Detecting In Vivo 13 C Magnetization Transfer Effect of Specific Enzyme Reactions in 1H Spectra" Resonance Imaging, Elsevier Science, Tarrytown, NY, US, vol. 26, No. 3, Dec. 11, 2007, XP022511977 ISSN: 0730-725X, pp. 413-419.

* cited by examiner

Figure 2  spin coupled spectrum of $^{13}C$

Figure 3 spin decoupled spectrum of $^{13}C$

Figure 4  decoupling sequence based on WALTZ 16, but with 0.2 ms pauses between each pulse

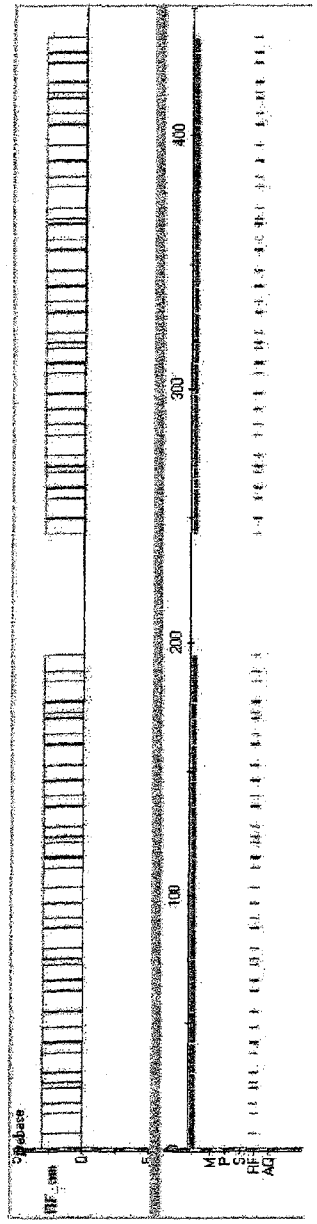
Figure 5
Nuclear Overhauser Effect (NOE) sequence based on the WALTZ 16 sequence but with short pauses between each block pulse within a supercycle and longer pauses between supercycles
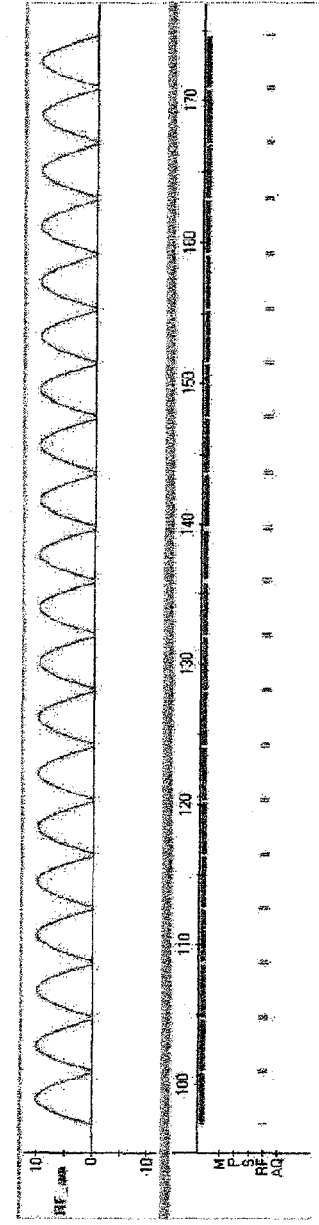
Figure 6 decoupling or Nuclear Overhauser Effect (NOE) sequence using smooth-shaped pulses rather than block pulses

BROADBAND DECOUPLING PULSE TRAINS WITH INTERLEAVED PAUSES FOR MAGNETIC RESONANCE SPECTROSCOPY

CROSS REFERENCE TO RELATED APPLICATIONS

This application claims the benefit of U.S. provisional application Ser. No. 61/139,781 filed Dec. 22, 2008, which is incorporated herein by reference.

The present application relates to the magnetic resonance spectroscopy arts. It finds particular application in conjunction with radiofrequency amplifiers for nuclear magnetic resonance spectroscopy for medical imaging employing broadband decoupling schemes.

Nuclear magnetic resonance spectroscopy (MRS) imaging allows for in vivo measurement of chemical composition based on the analysis of metabolites, such as rates of metabolic activity, in various human organs. Similar to MRI, MRS uses a static magnetic field and a radiofrequency (RF) pulse at a particular resonant frequency to observe the response of specific nuclei. The most commonly observed nuclei in vivo are $^1$H, $^{13}$C, $^{15}$N, $^{17}$O, $^{19}$F, $^{23}$Na, and $^{31}$P with most studies involving $^1$H, $^{13}$C and $^{31}$P.

A MRS system includes a permanent magnetic, electromagnet, or a superconducting electromagnet that produces the static magnetic field $B_0$. For an object placed within the $B_0$ field, nuclei with a net spin, i.e. has an odd atomic number, interact with one another and their surrounds to reach an ordered equilibrium state in which the nuclei spins preferentially align with the static magnetic field. The equilibrium is then disrupted by a second field $B_1$ in a transverse direction that oscillates at the Larmor frequency of the observed nuclei. This perturbation causes the aligned spins of the observed nuclei to rotate away from the $B_0$ plane toward the transverse $B_1$ plane. The Larmor frequency, which happens to be in the radiofrequency band, pulse $B_1$ is transmitted by a radiofrequency coil or antenna that is placed on or around the object of interest. The radiofrequency coil or antenna is connected to a transmitter that typically includes a frequency synthesizer that produces a digital envelope of RF frequencies and an amplifier. After the $B_1$ field is terminated, during a readout phase the observed nuclei begin to precess about the $B_0$ field and emit a magnetic resonance which induces a current in a receive coil or antenna. The current is then amplified, filtered, digitized, and stored for further processing.

The Larmor frequency is not constant among the observed nuclei. Due to differences in local chemical structure such as binding partners, bond lengths, and bond angles different observed nuclei of the observed nuclear species experience a slight variance or shift in their Larmor frequency. The shift occurs because electrons effectively shield the nucleus from the $B_0$ field causing the nuclei to experience different static magnetic fields. The frequency shift and the fundamental resonant frequency are directly proportional to the magnetic field strength; therefore, the ratio of the two values results in a field-independent, dimensionless value known as the chemical shift. The chemical shift is a frequency domain spectrum that is formed by converting the time-based Free Induction Decay (FID) signal to the frequency domain using various Fourier transformations. The spectrum has a frequency axis that corresponds to the chemical shift and an amplitude axis that corresponds to concentration. Along the frequency axis, specific nuclei give rise to a uniquely positioned single peak or multiple peaks. The area under the peak is directly related to the concentration of the specific nuclei.

Quantifying the area under the peaks presents a difficult task. Spectra are difficult to interpret due to overlapping or split resonances, distortion and signal loss from spin-spin coupling, and interference from species outside the region or volume of interest. Overlapping or split resonances can be resolved at higher field strengths due to increased chemical shift dispersion and reduced higher-order coupling. Spectroscopy at high field strengths further benefits sensitivity. Coupling issues are resolved by broadband decoupling schemes that improve resolution and sensitivity by collapsing multiplet structures due to the coupling of chemically bonded protons. Localization schemes such as single voxel spectroscopy (e.g. STEAM and PRESS) and multiple voxel spectroscopy (e.g. CSI) can reduce interference by suppression signals outside the region or volume of interest.

Decoupling is performed by exciting the region of interest by a radiofrequency pulse centered at the resonant frequency of the coupled species. The simplest decoupling scheme is a continuous wave (CW) at a single decoupling frequency; however, it is desirable to provide decoupling over a wider range of the spectrum, this is known as broadband decoupling. As noted above, to improve spectral resolution, i.e. chemical shift dispersion, the static field strength is increased but at the expense of an increased Larmor frequency and decoupling bandwidth. Broadband decoupling can still be achieved using existing decoupling schemes at higher field strengths, however it can lead to tissue heating, elevated specific absorption rate (SAR), and artifacts due to amplifier loading time. The RF amplifiers in high field, e.g. 7 Tesla or greater, MRI systems are designed to apply short pulses of high amplitude. The high field RF amplifiers have a short but finite loading time on the order of tens of microseconds. In broadband decoupling techniques, such as WALTZ-16, Garp, and the like, a train of composite inversion pulses periodically change characteristics, e.g., phase, frequently at short intervals. The short but finite loading time causes errors in the applied broadband RF field.

The present application provides a new and improved magnetic resonance spectroscopy apparatus and method which overcomes the above-referenced problems and others.

In accordance with one aspect, a method of high power broadband decoupling for magnetic resonance spectroscopy is provided. Magnetic resonance is induced in an observed nuclear species. A pulse train including a plurality of broadband decoupling radio frequency pulses configured to decouple a spectrum of a coupled nuclear species from the observed nuclear species is applied. Pauses are introduced between adjacent broadband decoupling radio frequency pulses of the decoupling pulse train. Magnetic resonance data from the observed nuclear species is acquired.

In accordance with another aspect, a magnetic resonance spectroscopy apparatus for high power broadband decoupling in magnetic resonance spectroscopy is provided. A magnet generates a static magnetic field. A magnetic resonance excitation system is configured to induce magnetic resonance in the observed species. A magnetic resonance data acquisition system is configured to acquire magnetic resonance data from the observed nuclear species. A decoupling system is configured to apply a decoupling pulse train including a plurality of broadband decoupling pulses configured to decouple a spectrum of a coupled nuclear species from the observed nuclear species. A decoupling delay generator is configured to introduce pauses between adjacent broadband decoupling pulses of the decoupling pulse train.

One advantage is that the broadband pulse train has pauses that are sufficiently long for the RF amplifier to recover yet are sufficiently short not to significantly affect the observed decoupling or the Nuclear Overhauser Effect (NOE).

Still further advantages of the present invention will be appreciated to those of ordinary skill in the art upon reading and understanding the following detailed description.

The invention may take form in various components and arrangements of components, and in various steps and arrangements of steps. The drawings are only for purposes of illustrating the preferred embodiments and are not to be construed as limiting the invention.

FIG. 5 illustrates an example of a Nuclear Overhauser Effect (NOE) sequence based on the WALTZ-16 sequence but with short pauses between each block pulse within a supercycle and longer pauses between supercycles; and FIG. 6 illustrates a decoupling or Nuclear Overhauser Effect (NOE) sequence using smooth-shaped pulses rather than block pulses.

Figure 1:
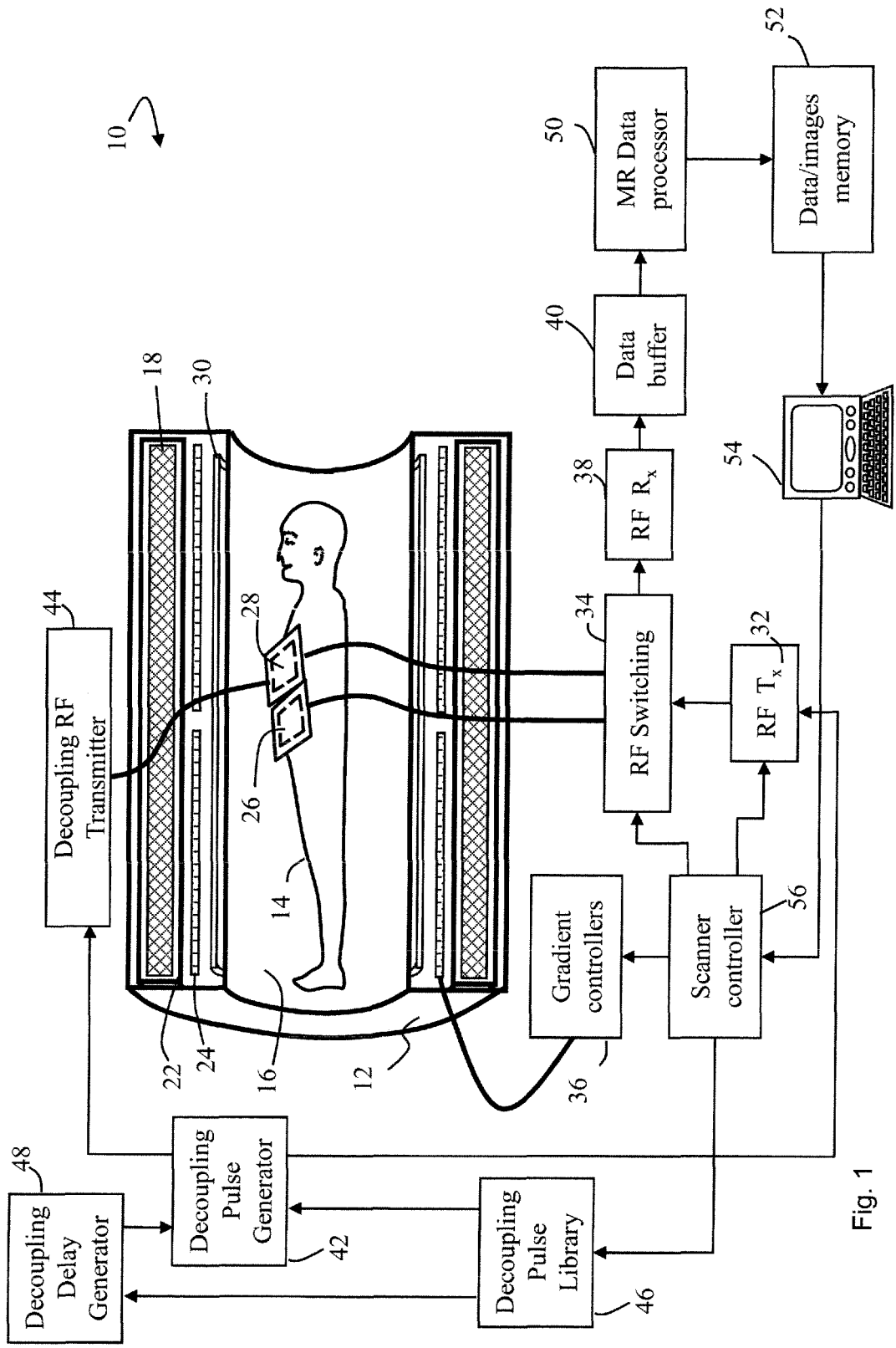
FIG. 1 is a diagrammatic diagram of a combined MRI and spectroscopy system.

With reference to FIG. 1, a magnetic resonance scanner 10 includes a scanner housing 12 in which a patient 14 or other observed subject is at least partially disposed. In a bore-type MR scanner embodiment; a protective insulating bore liner 16 of the scanner housing 12 optionally lines a cylindrical bore or opening of the scanner housing 12 inside of which the observed subject 14 is disposed. A main magnet 18 disposed in the scanner housing 12 generates a static ($B_0$) magnetic field in at least an observed region of the observed subject 14. Typically, the main magnet 18 is a persistent superconducting magnet surrounded by cryoshrouding 22, but resistive magnets, permanent magnets, and the like are also contemplated. In one embodiment, the main magnet 18 generates a main magnetic field of 7 Tesla, but higher and lower field strengths are also contemplated. Magnetic field gradient coils 24 are arranged in or on the housing 12 to superimpose selected magnetic field gradients on the main magnetic field in at least the observed region of the observed subject 14. Typically, the magnetic field gradient coils include coils for producing three orthogonal magnetic field gradients, such as x-gradients, y-gradients, and z-gradients. One or more local radio frequency coils 26, 28 are disposed in the bore of the scanner 10 and/or whole body RF coil 30 is disposed surrounding the bore. Although a bore-type MR system is illustrated, by way of example, the present concepts are also applicable to other types of MR systems, such as open MR systems, C-magnet systems, 4-poster magnet system, and the like. The same coil can be used to transmit and receive RF signals. Alternately, different coils are used for excitation, decoupling and reading. For example, the whole-body radio frequency coil 30 mounted in the scanner 10 can be used for magnetic resonance excitation at the magnetic resonance frequency of the observed nuclear species, while the local coil 26 can be used for reading the excited magnetic resonance. As another option, the local coil 26 or a second local coil 28 can be used to apply the decoupling pulse train and/or the NOE pulse train and the whole body coil can be used to generate the RF excitation pulses.

When performing spectroscopy, particularly single or multiple voxel spectroscopy, the applied radio frequency irradiation includes an excitation pulse used to selectively invert over a range of frequencies the spin state of the coupled nuclear species and a broadband interrupted pulse train to decouple it from the observed nuclear species during data readout.

In this Detailed Description, the example of $^{13}C$ is used as the observed nuclear species, and the example of $^1H$ is used as the chemically bonded or otherwise coupled nuclear species. However, it is to be appreciated that either or both of the observed nuclear species and the coupled nuclear species can be other species. For example, the observed nuclear species can be $^{15}N$, $^{17}O$, $^{19}F$, $^{23}Na$, or $^{31}P$ and the coupled nuclear species can be $^1H$, $^{13}C$, etc. In other configurations, $^1H$ is the observed nuclear species and the decoupled nuclear species are $^{13}C$, $^{15}P$, etc. For hetero-nuclear spectroscopy, the observed nuclear species and the coupled nuclear species typically have different atomic number (Z) values. For example, carbon has Z=6 while hydrogen has Z=1. The observed and coupled nuclear species can be naturally a part of the subject 14, or can be part of a substance that is administered to the subject 14 by injection, inhalation, ingestion, or so forth.

During magnetic resonance spectroscopy data acquisition, a radio frequency amplifier or transmitter 32 operating at the magnetic resonance frequency of the observed nuclear species (e.g., $^{13}C$) is coupled to the whole body coil 30 or a local coil 26 through radio frequency switching circuitry 34 to inject radio frequency excitation pulses at the magnetic resonance frequency of the observed nuclear species into the observed region of the observed subject 14 so as to excite magnetic resonance in spins of the observed nuclear species (e.g., $^{13}C$). Optionally, a magnetic field gradients controller 36 operates the magnetic field gradient coils 24 to spatially localize the magnetic resonance excitation to a slab, a voxel, a slice, or other localized region. The radio frequency amplifier 32 can also apply magnetic resonance manipulation pulses, e.g., inversion pulses at the magnetic resonance frequency to invert the excited magnetic resonance of the observed nuclear species, for example, to generate one or more spin echoes. The magnetic field gradient controller 36 operates the magnetic field gradient coils 24 to apply one or more spatial encoding magnetic field gradient pulses. During the magnetic resonance readout phase, the switching circuitry 34 disconnects the radio frequency amplifier 32 from the local coil 26, and connects a radio frequency receiver 38 to the local coil 26 to acquire magnetic resonance data from the observed region of the observed subject 14. The acquired magnetic resonance data are stored in a data buffer 40.

A decoupling pulse generator 42 generates radio frequency pulse configurations that are implemented by the RF amplifier 32 or by a second, decoupling radio frequency amplifier transmitter 44 operating a coil tuned to the resonance frequency of the coupled nuclei. For example, the whole body coil 30 can be multiply-tuned. Or one of the local coils, e.g., coil 28, can be tuned to the coupled nuclei frequency. The decoupling pulse generator generates a broadband decoupling signal having a broadband spectrum centered at about a magnetic resonance frequency of the coupled nuclear species (e.g., $^1H$). Typically, the whole body coil is used when higher power decoupling signals are advantageous. The broadband decoupling is typically applied during readout, such as during sampling of the spin echo or during free induction decay (FID) prior to the sampling, to decouple the observed nuclear species from the coupled nuclear species so as to provide improved spectral resolution from the magnetic resonance data of the observed nuclear species (e.g., $^{13}$C) for imaging, spectroscopy, or other applications. A decoupling pulse library 46 is configured with a plurality of decoupling pulse schemes. Decoupling pulse schemes, e.g. GARP, MLEV, WALTZ, are comprised of a contiguous train of RF pulses, e.g., with varying phases. The change in phase from pulse to pulse of the pulse train drives the coupled nuclear species such that coupling to the observed nuclear species is disrupted and/or the Nuclear Overhauser Effect is enhanced. The RF amplifier has an energy storage capacity that is exceeded if the decoupling pulse train is applied as a contiguous series of pulses resulting in RF droop. A decoupling delay generator 48 generates a delay signal that controls the decoupling pulse generator 42 to introduce pauses or gaps between pulses in the decoupling pulse train. The pauses are shorter than the coupling time between the observed nuclear species and the coupling nuclear species and longer than the phase change loading time of the decoupling RF amplifier 32. In this manner, the coupled nuclear species experience an effectively contiguous wave decoupling scheme while the decoupling RF transmitter experiences a short pause between phase changes. This pause, typically on the order of 0.05 msec-5.0 msec, allows the transmitter to operate for a greater duration, at a higher peak amplitude, at a lower specific absorption rate, and with reduced RF droop. A magnetic resonance data processor 50 performs processing of the magnetic resonance data to extract useful information. In imaging applications, the data processor 50 performs image reconstruction using a Fast Fourier transform or other image reconstruction algorithm along with the selected spatial encoding applied during generation of the magnetic resonance data. In spectroscopic applications, processing includes, for example, performing spectral fast Fourier transform operations to recover chemical shift and J-coupling data, e.g., for one or a plurality of voxels. For example, an image with a plurality of voxels can be defined with spectral data corresponding to each image voxel. Spectral data can be displayed in various ways such as displaying a corresponding spectral image in which each voxel is indicative of spectral information, highlighting a selected image voxel(s) to cause a pop-up display of the corresponding spectral data, or the like. The resulting processed data (e.g., images, spectra, or so forth) are suitably stored in a data/images memory 52, displayed on a user interface 54, printed, communicated over the Internet or a local area network, stored on a non-volatile storage medium, or otherwise used. In the example configuration illustrated in FIG. 1, the user interface 54 also interfaces a radiologist or other operator with a scanner controller 56 to control the magnetic resonance scanner 10 as described above. In other embodiments, a separate scanner control interface may be provided.

Figure 2:
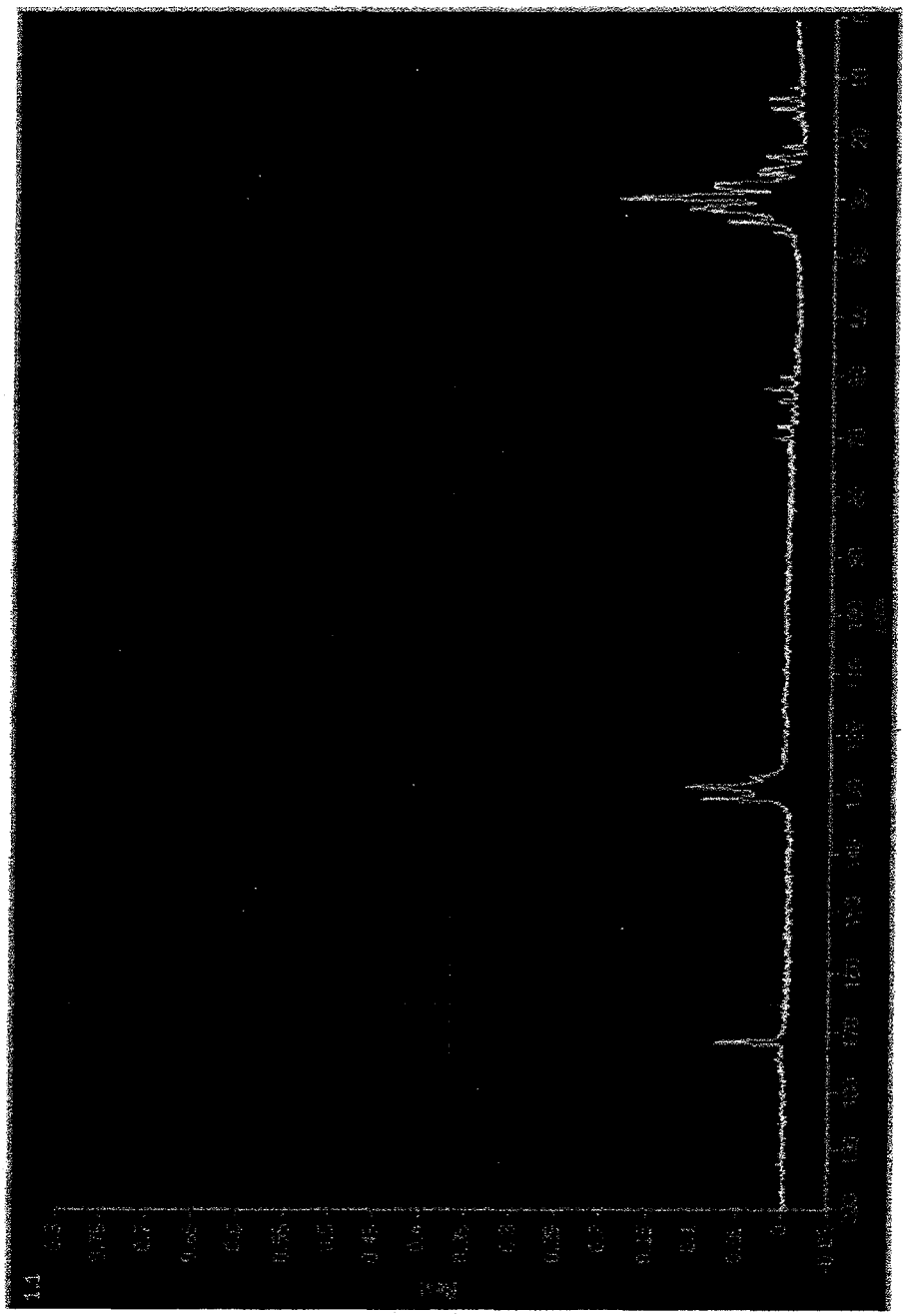
FIG. 2 illustrates a coupled spectrum of $^{13}C$ from a human leg with spin coupling in this example due to spin-½ protons (without the spin decoupling technique described in this application)
Figure 3:
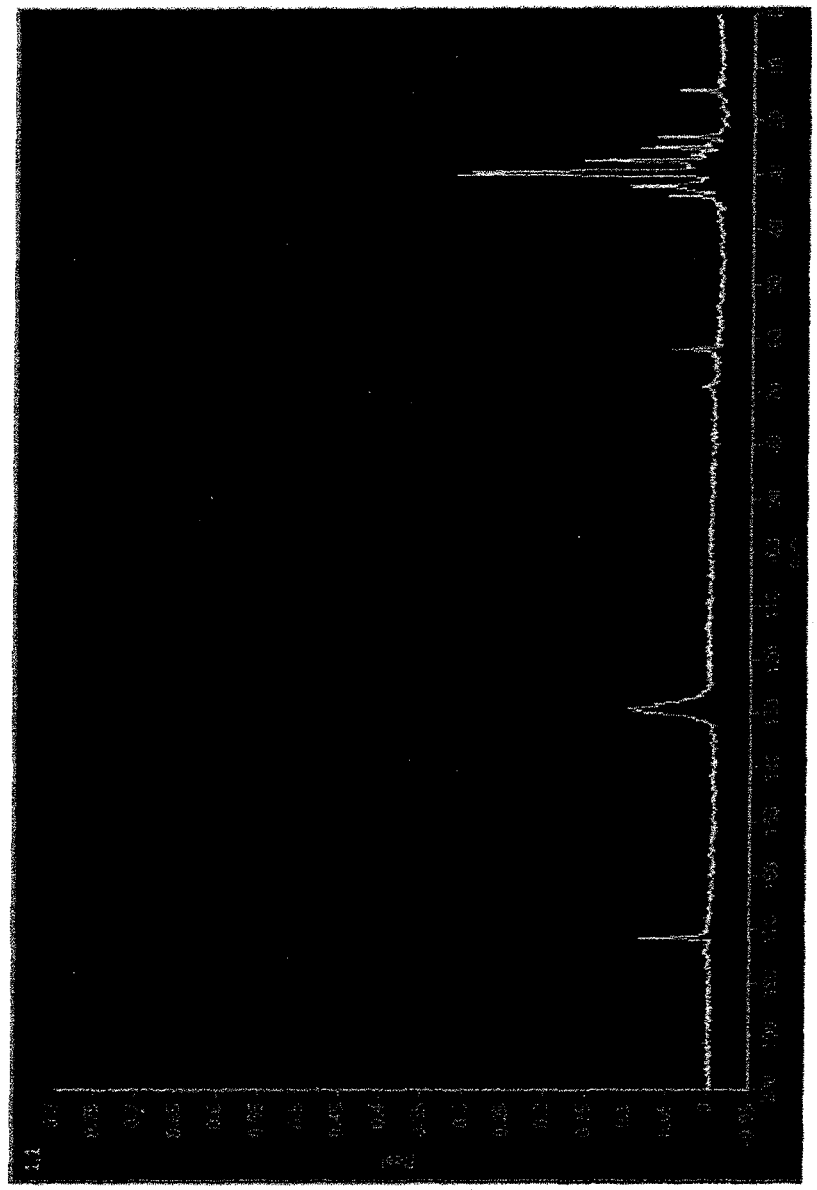
FIG. 3 illustrates the $^{13}C$ spectrum with spin decoupling in this example performed on the spin-½ protons as described herein.

With reference to FIGS. 2 and 3, more specifically FIG. 2 illustrates a chemical shift spectrum of a human leg in which $^{13}$C is the observed nuclear species without a decoupling scheme. FIG. 3 illustrates a chemical shift spectrum of a human leg in which $^{13}$C is the observed nuclear species and $^{1}$H is the decoupled nuclear species in a WALTZ-16 decoupling scheme, but with the pauses described above introduced between phase changes.

Figure 4:
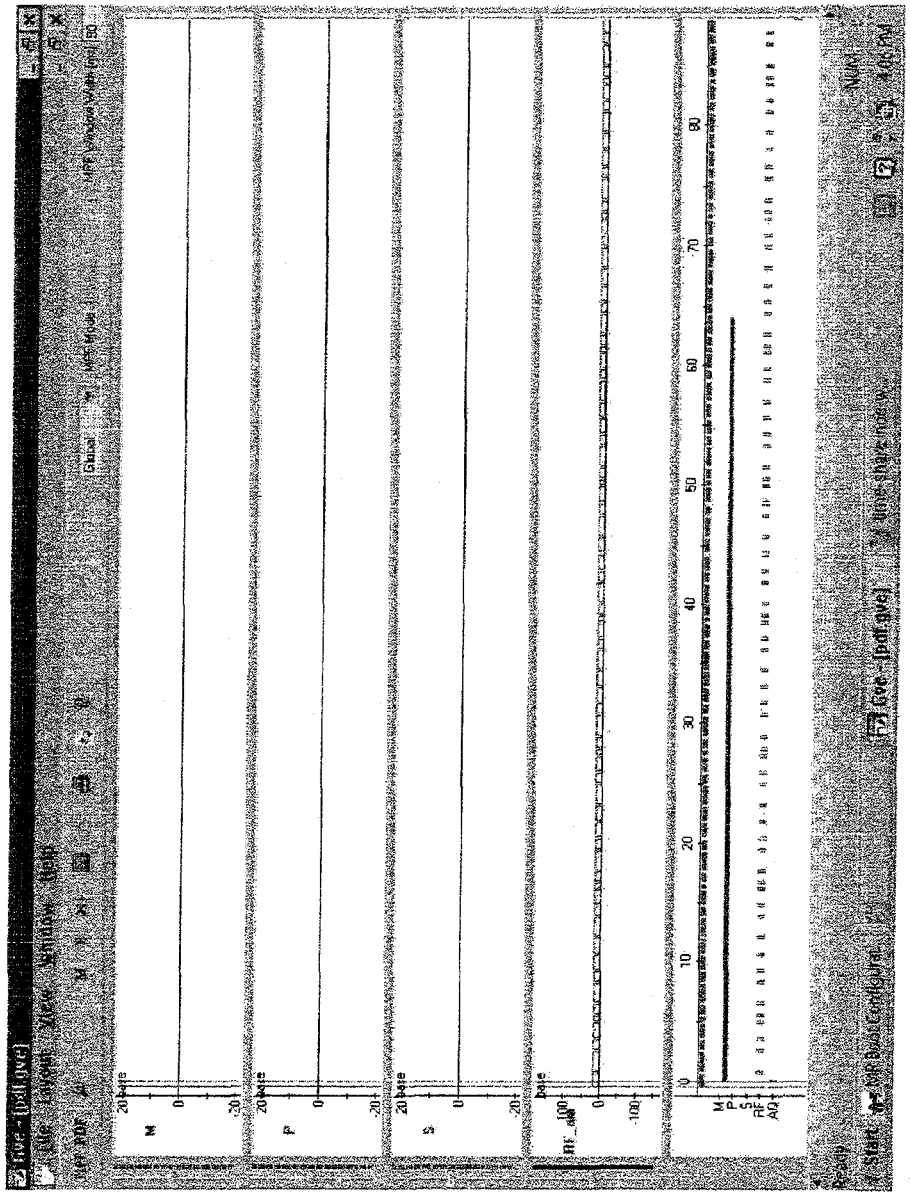
FIG. 4 is an example of a decoupling sequence based on WALTZ-16, but with 0.2 ms pauses between each pulse of the pulse train and pulses having a 15 µT amplitude.

With reference to FIG. 4, an example of WALTZ-16 decoupling with 0.2 ms pauses between each pulse of the decoupling pulse train. The decoupling pulses each have an amplitude of 15 μT for RF coils of clinically relevant geometries which exceeds the peak power amplitude available in CW operation for most RF amplifiers currently available for clinical use. This amplitude is available with the amplifier of the RF transmitter 32 used with the whole body coil of high field MRI systems.

FIG. 5 illustrates an example of the Nuclear Overhauser Effect (NOE) based on the WALTZ-16 decoupling scheme with a pause between each phase change of a supercycle and a longer pause between supercycles.

FIG. 6 illustrates decoupling or NOE using smooth-shaped pulses that provide an effective pause between pulses instead of the block pulses shown in FIG. 5.

This disclosure refers to preferred embodiments. Modifications and alterations may occur to others upon reading and understanding the preceding detailed description. It is intended that this disclosure be construed as including all such modifications and alterations insofar as they come within the scope of the appended claims or the equivalents thereof.

Having thus described the preferred embodiments, the invention is now claimed to be:

1. A method of high power broadband decoupling configured for a magnetic resonance scanner, comprising acts of:
   inducing in a static magnetic field of at least 7 Tesla a magnetic resonance in an observed nuclear species;
   applying at least two decoupling pulse train-trains each including a plurality of broadband decoupling radio frequency pulses configured to decouple a spectrum of a coupled nuclear species from the observed nuclear species;
   introducing a plurality of pauses between adjacent broadband decoupling radio frequency pulses of the at least two decoupling pulse trains;
   introducing a further pause between the at least two decoupling pulse trains, wherein the further pause is longer than at least one of the plurality of pauses
   acquiring magnetic resonance data of the observed nuclear species; and
   performing at least one of either:
      storing the acquired magnetic resonance data in a memory OR
      displaying the acquired magnetic resonance data in an image format.

2. The method according to claim 1, wherein the plurality of pauses are sufficiently short that decoupling is not sufficiently affected.

3. The method according to claim 1, wherein the at least two decoupling pulse trains enhance a Nuclear Overhauser Effect between the observed nuclear species and the coupled nuclear species.

4. The method according to claim 1, wherein the pulse train is amplified further comprising an act of:
   amplifying the at least two decoupling pulse trains by an RF amplifier whose energy storage capacity is exceeded when the at least two decoupling pulse trains are applied without the plurality of pauses, wherein the plurality of pauses have a length that provides a recovery time which is utilized by the RF amplifier.

5. The method according to claim 1, wherein the plurality of pauses are between 0.05 msec and 5.0 msec.

6. The method according to claim 5, wherein the plurality of pauses are about 0.2 msec.

7. The method according to claim 1, wherein the observed nuclear species is either 13C or 31p and the coupled nuclear species is 1H.

8. The method according to claim 1, wherein the at least two decoupling pulse trains include a WALTZ sequence.

9. The method according to claim 8, wherein the inducing magnetic resonance act includes acts of:
   aligning spins of the observed nuclear species in the static magnetic field of at least 7 T or greater; and perturbing the spins of the observed nuclear species with a radio frequency pulse centered at the resonant frequency of the observed nuclear species.

10. The method according to claim 4, wherein in each pulse train of the at least two decoupling pulse trains of the adjacent broadband decoupling radio frequency pulses have different phases, and each of the plurality of pauses are longer than a load change time of the amplifier.

11. A non-transitory computer readable medium comprising computer instructions which, when executed by a processor, configure the processor in order to perform acts of:
　inducing in a static magnetic field of at least 7 Tesla a magnetic resonance in an observed nuclear species;
　applying at least two decoupling pulse trains each including a plurality of broadband decoupling radio frequency pulses configured to decouple a spectrum of a coupled nuclear species from the observed nuclear species;
　introducing a plurality of pauses between adjacent broadband decoupling radio frequency pulses of the at least two decoupling pulse trains;
　introducing a further pause between the at least two decoupling pulse trains, wherein the further pause is longer than at least one of the plurality of pauses
　acquiring magnetic resonance data of the observed nuclear species; and
　performing at least one of either:
　　storing the acquired magnetic resonance data in a memory OR
　　displaying the acquired magnetic resonance data in an image format.

12. A magnetic resonance spectroscopy apparatus comprising:
　a magnet that generates a static magnetic field of at least 7 Tesla;
　a magnetic resonance excitation system configured to induce magnetic resonance in an observed nuclear species;
　a magnetic resonance data acquisition system configured to acquire magnetic resonance data of the observed nuclear species;
　a decoupling system configured to apply at least two decoupling pulse trains each including a plurality of broadband decoupling pulses that are configured to decouple a spectrum of a coupled species from the observed nuclear species;
　a decoupling delay generator configured to introduce pauses between adjacent broadband decoupling pulses of the at least two decoupling pulse trains and also configured to introduce a further pause between the at least two decoupling pulse trains, wherein the further pause is longer than at least one of the pauses introduced between adjacent broadband decoupling pulses of the at least two decoupling pulse trains;
　a processor acquiring magnetic resonance data of the observed nuclear species;
　a memory storing the magnetic resonance data acquired by the processor.

13. The magnetic resonance spectroscopy apparatus according to claim 12, wherein the introduced pauses are sufficiently short that at least one of: decoupling and a Nuclear Overhauser Effect enhancement, between the observed nuclear species and the coupled nuclear species, is not adversely affected.

14. The magnetic resonance spectroscopy apparatus according to claim 12, wherein the decoupling system includes an amplifier whose energy storage capacity is exceeded when the at least two decoupling pulse trains are applied without the introduced pauses, wherein the introduced pauses have a length that provides a recovery time which is utilized by the RF amplifier.

15. The magnetic resonance spectroscopy apparatus according to claim 12, wherein the magnet generates the static magnetic field of 7 T or greater.

16. The magnetic resonance spectroscopy apparatus according to claim 12, wherein the decoupling system includes a decoupling pulse train library that stores a plurality of contiguous decoupling pulse trains, including WALTZ pulse trains, GARP pulse trains, and MLEV pulse trains, from which a selection of one of a plurality of contiguous decoupling pulse trains is made; whereby the selection is utilized in order to provide the insertion of the introduced pauses, by the decoupling delay generator, prior to being amplified by an amplifier and then applied to the coupled nuclear species.

17. The magnetic resonance spectroscopy apparatus according to claim 12, further including a magnetic field gradient system which applies magnetic field gradients whereby the acquired magnetic resonance data is spatially encoded.

18. The magnetic resonance spectroscopy apparatus according to claim 17, further including an MR data processor which processes the acquired magnetic resonance data in order to generate spectral information within each of a plurality of voxels.

19. A magnetic resonance spectroscopy apparatus of high power broadband decoupling configured for magnetic resonance spectroscopy, the magnetic resonance apparatus comprising:
　means for inducing in a static magnetic field of at least 7 Tesla a magnetic resonance in an observed nuclear species;
　means for applying at least two decoupling pulse trains including a plurality of broadband decoupling radio frequency pulse configured to decouple a spectrum of a coupled nuclear species form the observed nuclear species;
　means for introducing pauses between adjacent broadband decoupling radio frequency pulses of the at least two decoupling pulse trains and introducing a further pause between the at least two decoupling pulse trains, wherein the further pause is longer than at least one of the pauses introduced between adjacent broadband decoupling pulses of the at least two decoupling pulse trains
　means for acquiring magnetic resonance data of the observed nuclear species; and
　means for performing at least one of either:
　　storing the acquired magnetic resonance data, OR
　　displaying the acquired magnetic resonance data.

* * * * *